United States Patent
Andree et al.

(10) Patent No.: US 6,780,821 B1
(45) Date of Patent: Aug. 24, 2004

(54) SUBSTITUTED PHENYL URACILS

(75) Inventors: Roland Andree, Langenfeld (DE); Mark Wilhelm Drewes, Langenfeld (DE); Dieter Feucht, Monheim (DE); Rolf Pontzen, Leichlingen (DE); Ingo Wetcholowsky, Estancia Marambaia (BR); Hans-Georg Schwarz, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/720,892
(22) PCT Filed: Jul. 2, 1999
(86) PCT No.: PCT/EP99/04585
§ 371 (c)(1),
(2), (4) Date: Jun. 20, 2002
(87) PCT Pub. No.: WO00/02866
PCT Pub. Date: Jan. 20, 2000

(30) Foreign Application Priority Data

Jul. 9, 1998 (DE) .......................................... 198 30 693
Nov. 23, 1998 (DE) .......................................... 198 53 864

(51) Int. Cl.$^7$ ........................ A01N 43/54; C07D 239/52
(52) U.S. Cl. ........................ 504/243; 544/309; 544/311; 544/312; 544/313; 544/314
(58) Field of Search ........................ 504/243; 544/309, 544/311, 312, 313, 314

(56) References Cited

U.S. PATENT DOCUMENTS

| | | | |
|---|---|---|---|
| 4,812,164 A | 3/1989 | Wenger et al. | 71/92 |
| 4,859,229 A | 8/1989 | Wenger et al. | 71/92 |
| 4,979,982 A | 12/1990 | Brouwer et al. | 71/92 |
| 5,084,084 A | 1/1992 | Satow et al. | 71/92 |
| 5,116,404 A | 5/1992 | Ishii et al. | 71/92 |
| 5,127,935 A | 7/1992 | Satow et al. | 71/92 |
| 5,134,144 A | 7/1992 | Brouwer et al. | 514/274 |
| 5,154,755 A | 10/1992 | Satow et al. | 71/92 |
| 5,169,430 A | 12/1992 | Strunk et al. | 71/92 |
| 5,183,492 A | 2/1993 | Suchy et al. | 504/243 |
| 5,266,554 A | 11/1993 | Suchy et al. | 504/243 |
| 5,280,010 A | 1/1994 | Enomoto et al. | 504/243 |
| 5,356,863 A | 10/1994 | Satow et al. | 504/243 |
| 5,486,610 A | 1/1996 | Strunk et al. | 544/311 |
| 6,333,296 B1 * | 12/2001 | Pulman et al. | 504/243 |
| 6,451,740 B2 * | 9/2002 | Tohyama et al. | 504/243 |
| 6,455,469 B1 * | 9/2002 | Crosby et al. | 504/127 |

FOREIGN PATENT DOCUMENTS

| | | |
|---|---|---|
| DE | 195 27 570 | 1/1997 |
| WO | 93/14073 | 7/1993 |
| WO | 98/41093 | 9/1998 |

* cited by examiner

*Primary Examiner*—Richard L. Raymond
(74) *Attorney, Agent, or Firm*—Richard E.L. Henderson

(57) ABSTRACT

The invention relates to new substituted phenyluracils of the general formula (I)

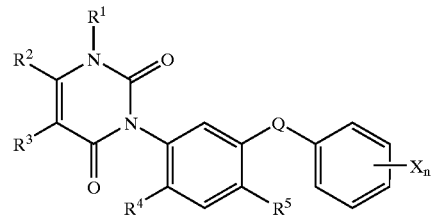

(I)

in which
n, Q, $R^1$, $R^2$, $R^3$, $R^4$, $R^5$ and X have the meanings given in the description,
to process and new intermediates for their preparation, and to their use as herbicides.

13 Claims, No Drawings

SUBSTITUTED PHENYL URACILS

The invention relates to new substituted phenyluracils, to processes and new intermediates for their preparation, and to their use as herbicides.

Certain substituted aryluracils have already been disclosed in the (patent) literature (cf. EP-A-255047, EP-A-260621, EP-A408382, EP-A-438209, EP-A473551, EP-A-517181, EP-A-563384, WO-A-91/00278, WO-A-91/07393, WO-A-93/14073, WO-A-98/41093, U.S. Pat. Nos. 4,979,982, 5,084,084, 5,127,935, 5,154,755, 5,169,430, 5,486,610, 5,356,863). However, these compounds have not gained any particular importance to date.

There have now been found new substituted phenyluracils of the general formula (I)

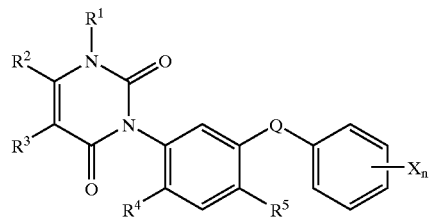

(I)

in which n represents the numbers 0, 1, 2, 3, 4 or 5,

Q represents O (oxygen), S (sulphur), SO, $SO_2$, NH or N(alkyl), $R^1$ represents hydrogen, amino or optionally substituted alkyl, $R^2$ represents carboxyl, cyano, carbamoyl, thiocarbamoyl or in each case optionally substituted alkyl or alkoxycarbonyl, $R^3$ represents hydrogen, halogen or optionally substituted alkyl, $R^4$ represents hydrogen, cyano, carbarmoyl, thiocarbamoyl or halogen, $R^5$ represents cyano, carbamoyl, thiocarbamoyl, halogen or in each case optionally substituted alkyl or alkoxy, and X represents hydroxyl, mercapto, amino, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino, alkylcarbonyl, alkoxycarbonyl, alkylaminocarbonyl, dialkylaminocarbonyl, alkylcarbonyloxy, alkoxycarbonyloxy, alkylaminocarbonyloxy, dialkylaminocarbonyloxy, phenylcarbonyloxy, alkylcarbonylamino, alkoxycarbonylamino, alkylsulphonylamino, alkenyl, alkenyloxy, alkenyloxycarbonyl, alkinyl, alkinyloxy or alkinyloxycarbonyl, where, in the event that n is greater than 1, X in the individual compounds which are possible can also have different meanings from those indicated.

In the definitions, the hydrocarbon chains, such as alkyl—also in connection with hetero atoms such as in alkoxy—are in each case straight-chain or branched.

In as far as the compounds of the general formula (I) according to the invention contain substituents with asymmetric carbon atoms, the invention relates in each case to the R enantiomers and the S enantiomers and to any mixtures of these enantiomers, in particular the racemates.

n preferably represents the numbers 0, 1, 2, 3 or 4;

Q preferably represents O (oxygen), S (sulphur), SO, $SO_2$, NH or N($C_1$–$C_4$-alkyl);

$R^1$ preferably represents hydrogen, amino, or $C_1$–$C_4$-alkyl which is optionally substituted by cyano, carboxyl, fluorine, chlorine, $C_1$–C4-alkoxy or $C_1$–$C_4$-alkoxycarbonyl;

$R^2$ preferably represents carboxyl, cyano, carbamoyl, thiocarbamoyl, or represents $C_1$–$C_4$-alkyl or $C_1$–$C_4$-alkoxy-carbonyl, each of which is optionally substituted by cyano, fluorine, chlorine or $C_1$–$C_4$-alkoxy;

$R^3$ preferably represents hydrogen, fluorine, chlorine, bromine, or represents $C_1$–$C_4$-alkyl which is optionally substituted by fluorine or chlorine;

$R^4$ preferably represents hydrogen, cyano, carbamoyl, thiocarbamoyl, fluorine, chlorine or bromine;

$R^5$ preferably represents cyano, carbamoyl, thiocarbamoyl, fluorine, chlorine, bromine, or represents $C_1$–$C_4$-alkyl or $C_1$–$C_4$-alkoxy, each of which is optionally substituted by fluorine and/or chlorine;

X preferably represents hydroxyl, mercapto, amino, nitro, cyano, carboxyl, carbamoyl, thiocarbamoyl, fluorine, chlorine, bromine, iodine, or represents alkyl, alkoxy, alkylthio, alkylsulphinyl, alkylsulphonyl or alkylamino, each of which has 1 to 6 carbon atoms and each of which is optionally substituted by hydroxyl, cyano, carboxyl, carbamoyl, fluorine, chlorine, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl- carbonyl, $C_1$–$C_4$-alkoxy-carbonyl, $C_2$–$C_4$-alkenyl-oxycarbonyl, $C_2$–$C_4$-alkinyl-oxycarbonyl, $C_1$–C4-alkylamino-carbonyl, di-($C_1$–$C_4$-alkyl)amino-carbonyl, phenoxycarbonyl, benzyloxycarbonyl, phenylaminocarbonyl or benzylaminocarbonyl, or represents dialkylamino having 1 to 6 carbon atoms in each of the alkyl groups, or represents alkylcarbonyl, alkoxycarbonyl, alkylaminocarbonyl, alkylcarbonyloxy, alkoxycarbonyloxy or alkylaminocarbonyloxy, each of which has 1 to 6 carbon atoms in the alkyl groups and each of which is optionally substituted by cyano, fluorine, chlorine, bromine or $C_1$–$C_4$-alkoxy, or represents dialkylaminocarbonyl or dialkylaminocarbonyloxy, each of which has 1 to 6 carbon atoms in the alkyl groups, or represents phenylcarbonyloxy, or represents alkylcarbonylamino, alkoxycarbonylamino, alkylsulphonylamino, each of which is optionally substituted by fluorine, chlorine or bromine, or represents alkenyl, alkenyloxy, alkenyloxycarbonyl, alkinyl, alkinyloxy or alkinyloxycarbonyl, each of which has up to 6 carbon atoms and each of which is optionally substituted by cyano, carboxyl, fluorine, chlorine, bromine or $C_1$–$C_4$-alkoxy-carbonyl;

n especially preferably represents the numbers 1, 2 or 3;

Q especially preferably represents O (oxygen), S (sulphur), SO, $SO_2$, NH or N($CH_3$);

$R^1$ especially preferably represents hydrogen, amino, or represents methyl, ethyl, n- or i-propyl, each of which is optionally substituted by cyano, fluorine, chlorine, methoxy or ethoxy;

$R^2$ especially preferably represents carboxyl, cyano, carbamoyl, thiocarbamoyl, or represents methyl, ethyl, n- or i-propyl, methoxycarbonyl, ethoxycarbonyl, n- or i-propoxycarbonyl, each of which is optionally substituted by cyano, fluorine, chlorine, methoxy or ethoxy;

$R^3$ especially preferably represents hydrogen, fluorine, chlorine, bromine, or represents methyl or ethyl, each of which is optionally substituted by fluorine and/or chlorine;

$R^4$ especially preferably represents hydrogen, fluorine or chlorine;

$R^5$ especially preferably represents cyano, carbamoyl, thiocarbamoyl, fluorine, chlorine, bromine, methyl or trifluoromethyl;

X especially preferably represents hydroxyl, mercapto, amino, nitro, cyano, carboxyl, carbamoyl, thiocarbamoyl, fluorine, chlorine, bromine, or represents methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethylsulphinyl, methylsulphonyl, ethylsulphonyl, methylamino, ethylamino, n- or i-propylamino, n-, i-, s- or t-butylamino, each of which is optionally substituted by cyano, carboxyl, carbamoyl, fluorine, chlorine, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, allyloxycarbonyl, 1-buten-3-yl-oxy-carbonyl, 2-buten-4-yl-oxy-carbonyl, propargyloxycarbonyl, 1-butin-3-yl-oxy-carbonyl, 2-butin-4-yl-oxy-carbonyl, methylaminocarbonyl, ethylaminocarbonyl, n- or i-propylamino-carbonyl, dimethylaminocarbonyl, diethylamino-carbonyl, phenoxycarbonyl, benzyloxycarbonyl, phenylaminocarbonyl or benzylaminocarbonyl, or represents dimethylamino or diethylamino, or represents acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, each of which is optionally substituted by cyano, fluorine, chlorine, methoxy, ethoxy, n- or i-propoxy, or represents dimethylaminocarbonyl, diethylaminocarbonyl, dimethylaminocarbonyloxy or diethylaminocarbonyloxy, or represents phenylcarbonyloxy, or represents acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, each of which is optionally substituted by fluorine or chlorine, or represents ethenyl, propenyl, propenyloxy, propenyloxycarbonyl, ethinyl, propinyl, propinyloxy or propinyloxycarbonyl, each of which is optionally substituted by cyano, carboxyl, fluorine, chlorine, methoxycarbonyl or ethoxycarbonyl.

Preferred according to the invention are those compounds of the formula (I) in which there exists a combination of the meanings mentioned above as being preferred.

Especially preferred according to the invention are those compounds of the formula (I) in which there exists a combination of the meanings mentioned above as being especially preferred.

A very especially preferred group are the compounds of the formula (IA)

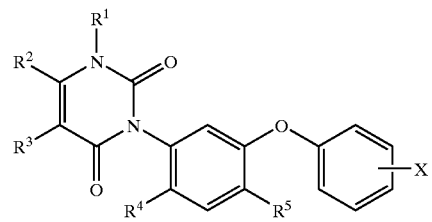

in which
- $R^1$ represents hydrogen, amino or methyl,
- $R^2$ represents trifluoromethyl, chlorodifluoromethyl, difluoromethyl or pentafluoroethyl,
- $R^3$ represents hydrogen, chlorine or methyl,
- $R^4$ represents hydrogen, fluorine or chlorine,
- $R^5$ represents cyano or thiocarbamoyl, and
- X represents hydroxyl, mercapto, amino, nitro, cyano, carboxyl, carbamoyl, thiocarbamoyl, fluorine, chlorine, bromine, or represents methyl, ethyl, methoxy, ethoxy, methylthio, ethylthio, methoxycarbonyl or ethoxycarbonyl, each of which is optionally substituted by cyano, carboxyl, carbamoyl, fluorine, chlorine, methoxy, ethoxy, n- or i-propoxy, methoxycarbonyl, ethoxycarbonyl, n- or i-propoxy-carbonyl, allyloxycarbonyl, propargyloxy-carbonyl, 1-buten-3-yl-oxy-carbonyl, 2-buten-4-yl-oxy-carbonyl, propargyl-oxycarbonyl, 1-butin-3-yl-oxy-carbonyl, 2-butin-4-yl-oxy-carbonyl, methyl-aminocarbonyl, ethylaminocarbonyl, n- or i-propylamino-carbonyl, dimethyl-aminocarbonyl, diethylamino-carbonyl, phenoxycarbonyl, benzyloxycarbonyl, phenylaminocarbonyl or benzylaminocarbonyl, or represents ethenyl which is substituted by methoxycarbonyl or ethoxycarbonyl.

Another very especially preferred group are those compounds of the formula (IA) in which
- $R^1$ represents methyl,
- $R^2$ represents trifluoromethyl, chlorodifluoromethyl, difluoromethyl or pentafluoroethyl,
- $R^3$ represents hydrogen, chlorine or methyl,
- $R^4$ represents hydrogen, fluorine or chlorine,
- $R^5$ represents fluorine, chlorine, bromine or trifluoromethyl, and
- X represents hydroxyl, mercapto, amino, nitro, cyano, carboxyl, carbamoyl, thiocarbamoyl, fluorine, chlorine, bromine, or represents methyl, ethyl, methoxy, ethoxy, methylthio, ethylthio, methoxycarbonyl or ethoxycarbonyl, each of which is optionally substituted by cyano, carboxyl, carbamoyl, fluorine, chlorine, methoxy, ethoxy, n- or i-propoxy, methoxycarbonyl, ethoxycarbonyl, n- or i-propoxy-carbonyl, allyloxycarbonyl, propargyloxy-carbonyl, 1-buten-3-yl-oxy-carbonyl, 2-buten-4-yl-oxy-carbonyl, propargyl-oxycarbonyl, 1-butin-3-yl-oxy-carbonyl, 2-butin-4-yl-oxy-carbonyl, methyl-aminocarbonyl, ethylaminocarbonyl, n- or i-propylamino-carbonyl, dimethyl-aminocarbonyl, diethylamino-carbonyl, phenoxycarbonyl, benzyloxycarbonyl, phenylaminocarbonyl or benzylaminocarbonyl, or represents ethenyl which is substituted by methoxycarbonyl or ethoxycarbonyl.

Another very especially preferred group are those compounds of the formula (IA) in which $R^1$ represents hydrogen, amino or methyl, $R^2$ represents carboxyl, cyano, carbamoyl, thiocarbamoyl, methoxycarbonyl or ethoxycarbonyl, $R^3$ represents hydrogen, chlorine or methyl, $R^4$ represents hydrogen, fluorine or chlorine, $R^5$ represents cyano, thiocarbamoyl, fluorine, chlorine, bromine or trifluoromethyl, and X represents hydroxyl, mercapto, amino, nitro, cyano, carboxyl, carbamoyl, thiocarbamoyl, fluorine, chlorine, bromine, or represents methyl, ethyl, methoxy, ethoxy, methylthio, ethylthio, methoxycarbonyl or ethoxycarbonyl, each of which is optionally substituted by cyano, carboxyl, carbamoyl, fluorine, chlorine, methoxy, ethoxy, n- or i-propoxy, methoxycarbonyl, ethoxycarbonyl, n- or i-propoxy-carbonyl, allyloxycarbonyl, propargyloxy-carbonyl, 1-buten-3-yl-oxy-carbonyl, 2-buten-4-yl-oxy-carbonyl, propargyl-oxycarbonyl, 1-butin-3-yl-oxy-carbonyl, 2-butin-4-yl-oxy-carbonyl, methyl-aminocarbonyl, ethylaminocarbonyl, n- or i-propylamino-carbonyl, dimethyl-aminocarbonyl, diethylamino-carbonyl, phenoxycarbonyl, benzyloxycarbonyl, phenylaminocarbonyl or benzylaminocarbonyl, or represents ethenyl which is substituted by methoxycarbonyl or ethoxycarbonyl.

The definitions of the radicals given above, either in general or in preferred ranges, apply not only to the end products of the formula (I), but also, correspondingly, to the starting materials or intermediates required in each case for their preparation. These definitions of radicals can be combined with each other as desired, that is to say combinations between the preferred ranges mentioned are also possible.

Examples of the compounds of the general formula (I) according to the invention are given in the groups which follow.

Group 1

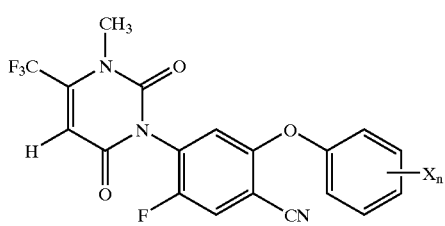

$X_n$ has the meanings mentioned in the list which follows:

2-hydroxyl, 3-hydroxyl, 4-hydroxyl, 2-cyano, 3-cyano, 4-cyano, 2-carboxy, 3-carboxyl, 4-carboxyl, 2-fluoro, 3-fluoro, 4-fluoro, 2,3-difluoro, 2,4-difluoro, 2,5-difluoro, 2,6-difluoro, 3,4-difluoro, 3,5-difluoro, 2-chloro, 3-chloro, 4-chloro, 2,3-dichloro, 2,4-dichloro, 2,5-dichloro, 2,6-dichloro, 3,4-dichloro, 3,5-dichloro, 2-bromo, 3-bromo, 4-bromo, 2-methyl, 3-methyl, 4-methyl, 2,3-dimethyl, 2,4-dimethyl, 2,5-dimethyl, 2,6-dimethyl, 3,4-dimethyl, 3,5-dimethyl, 2-trifluoro-methyl, 3-trifluoromethyl, 4-trifluoromethyl, 2-methoxy, 3-methoxy, 4-methoxy, 2,4-dimethoxy, 2,5-dimethoxy, 2,6-dimethoxy, 3,4-dimethoxy, 2-difluoromethoxy, 4-difluoromethoxy, 2-trifluoromethoxy, 4-trifluoromethoxy, 4-ethoxy, 4-methylthio, 4-ethylthio, 4-methoxycarbonyl, 4-ethoxycarbonyl, 4-carboxymethoxy, 4-methoxy-carbonylmethoxy, 4-ethoxycarbonylmethoxy, 4-n-propoxycarbonylmethoxy, 4-i-propoxycarbonylmethoxy, 4-(1-carboxyethoxy), 4-(1-(methoxycarbonyl)ethoxy), 4(1-(ethoxycarbonyl)ethoxy), 4-(1-(n-propoxycarbonyl)ethoxy), 4-(1-(i-propoxy-carbonyl)ethoxy), 4-(allyloxycarbonylmethoxy), 4-(1-(allyloxycarbonylethoxy), 4-(propargyloxycarbonylmethoxy), 4-(1-(propargyloxycarbonyl)ethoxy), 4-(benzyl-oxycarbonylmethoxy), 4-(1-(benzyloxycarbonylethoxy), 4-(aminocarbonylmethoxy), 4-(methylaminocarbonylmethoxy), 4-(ethylaminocarbonylmethoxy), 4-(n-propylaminocarbonylmethoxy), 4-(i-propylaminocarbonylmethoxy), 4-(dimethylaminocarbonylmethoxy), 4-(1-(methylaminocarbonyl)ethoxy), 4-(1-ethylaminocarbonyl)ethoxy), 4-(1-(n-propylaminocarbonyl)ethoxy), 4-(1-(i-propylaminocarbonyl)ethoxy), 4-(1-(dimethylaminocarbonyl)ethoxy), 4-(2-methoxycarbonyl-ethenyl), 4-(2-ethoxycarbonyl-ethenyl).

Group 2

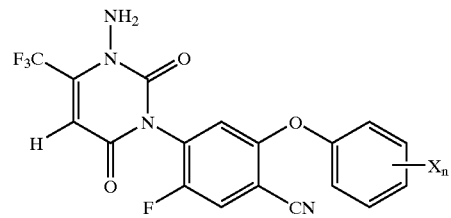

$X_n$ has the meanings mentioned above in Group 1.

Group 3

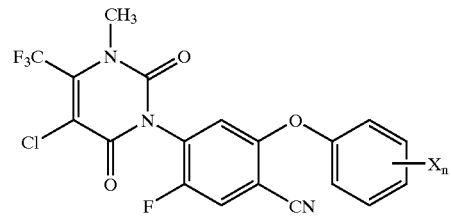

$X_n$ has the meanings mentioned above in Group 1.

Group 4

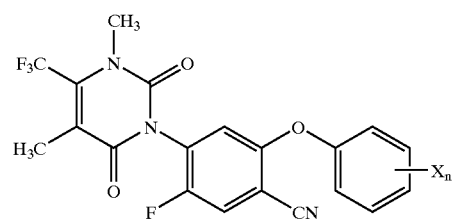

$X_n$ has the meanings mentioned above in Group 1.

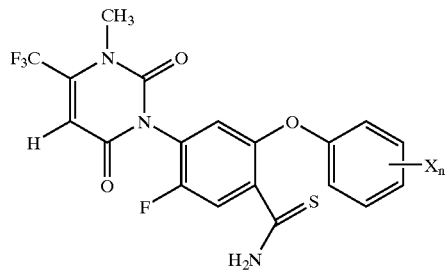

Group 5

$X_n$ has the meanings mentioned above in Group 1.

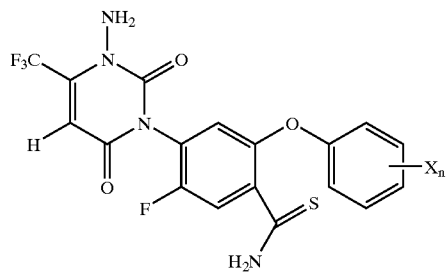

Group 6

$X_n$ has the meanings mentioned above in Group 1.

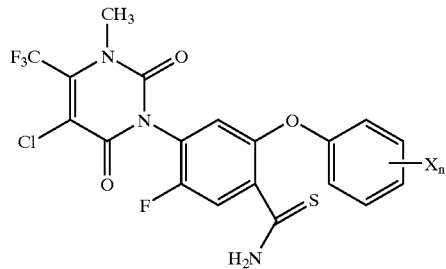

Group 7

$X_n$ has the meanings mentioned above in Group 1.

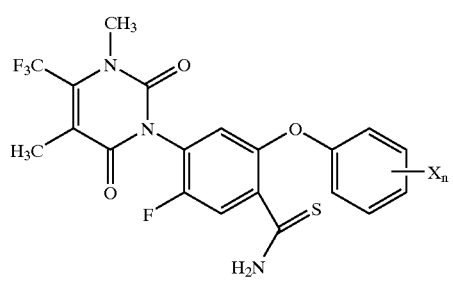

Group 8

$X_n$ has the meanings mentioned above in Group 1.

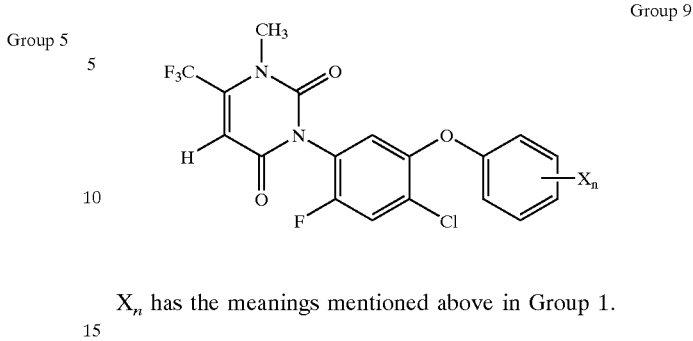

Group 9

$X_n$ has the meanings mentioned above in Group 1.

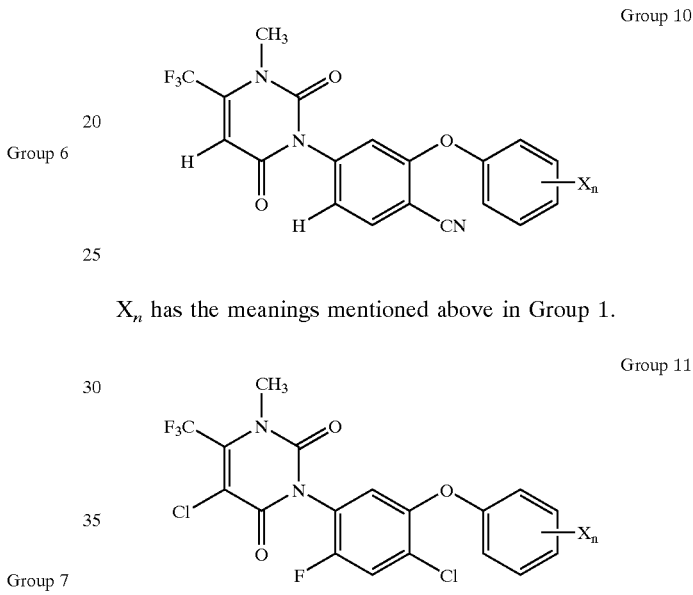

Group 10

$X_n$ has the meanings mentioned above in Group 1.

Group 11

$X_n$ has the meanings mentioned above in Group 1.

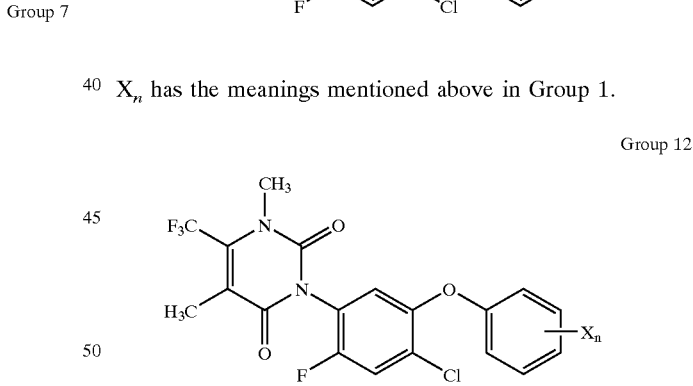

Group 12

$X_n$ has the meanings mentioned above in Group 1.

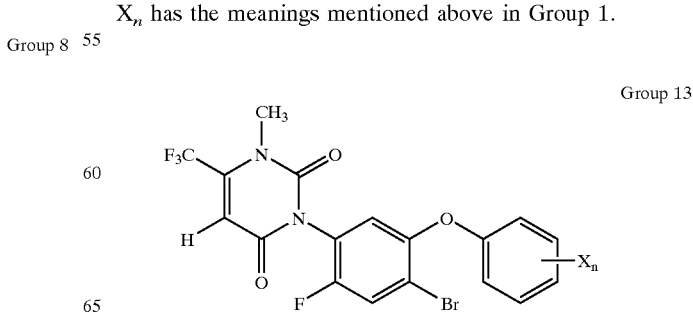

Group 13

X$_n$ has the meanings mentioned above in Group 1.

Group 14

[Structure: phenyluracil with CH$_3$, F$_3$C, F, CF$_3$, O-phenyl-X$_n$ substituents]

X$_n$ has the meanings mentioned above in Group 1.

Group 15

[Structure: phenyluracil with CH$_3$, NC, F, CN, O-phenyl-X$_n$ substituents]

X$_n$ has the meanings mentioned above in Group 1.

The new substituted phenyluracils of the general formula (I) have interesting biological properties. They are distinguished, in particular, by a potent herbicidal activity.

The new substituted phenyluracils of the general formula (I) are obtained when (a) halogenophenyluracils of the general formula (II)

(II)

[Structure with R$^1$, R$^2$, R$^3$, R$^4$, R$^5$, X$^1$]

in which

R$^1$, R$^2$, R$^3$, R$^4$ and R$^5$ have the abovementioned meaning and

X$^1$ represents halogen are reacted with aryl compounds of the general formula (III)

(III)

[Structure: H–Q–phenyl–X$_n$]

in which n, Q and X have the abovementioned meaning or with metal salts of compounds of the general formula (III)

if appropriate in the presence of a reaction auxiliary and if appropriate in the presence of a diluent, or when (b) aminoalkenoic esters of the general formula (IV)

(IV)

[Structure with NH$_2$, R$^2$, R$^3$, OR]

in which

R$^2$ and R$^3$ have the abovementioned meaning and

R represents alkyl, aryl or arylalkyl are reacted with aryl isocyanates of the general formula (V)

(V)

[Structure: OCN-phenyl(R$^4$,R$^5$)-Q-phenyl-X$_n$]

in which n, Q, R$^4$, R$^5$ and X have the abovementioned meaning or with arylurethanes (arylcarbamates) of the general formula (VI)

(VI)

[Structure: RO-C(=O)-NH-phenyl(R$^5$,R$^6$)-Q-phenyl-X$_n$]

in which n, Q, R$^5$, R$^6$ and X have the abovementioned meaning and

R represents alkyl, aryl or arylalkyl, if appropriate in the presence of a reaction auxiliary and if appropriate in the presence of a diluent, or when (c) N-aryl-1-alkoxycarbonylamino-maleimides of the general formula (VII)

(VII)

[Structure: maleimide with OR', R$^3$, N-phenyl(R$^4$,R$^5$)-Q-phenyl-X$_n$]

in which n, Q, R$^3$, R$^4$ R$^5$ and X have the abovementioned meaning and

R' represents alkyl are reacted with a metal hydroxide in the presence of water and if appropriate in the presence of an organic solvent, or when (d) substituted phenyluracils of the general formula (Ia)

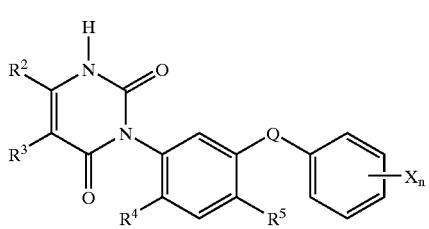
(Ia)

in which n, Q, $R^2$, $R^3$, $R^4$, $R^5$ and X have the abovementioned meaning are reacted with 1-aminooxy-2,4-dinitro-benzene or with alkylating agents of the general formula (VIII)

$$X^2-A^1 \quad (VIII)$$

in which $A^1$ represents optionally substituted alkyl and $X^2$ represents halogen or the group —O—$SO_2$—O—$A^1$, if appropriate in the presence of a reaction auxiliary and if appropriate in the presence of a diluent, and, if appropriate, electrophilic or nucleophilic or oxidation and reduction reactions are subsequently carried out in the customary manner within the scope of the definition of the substituents.

The compounds of the general formula (I) can be converted into other compounds of the general formula (I) in accordance with the above definition by customary methods, for example by esterification or hydrolysis (for example X: $OCH_2COOH \rightarrow OCH_2COOC_2H_5$, $OCH(CH_3)COOCH_3 \rightarrow OCH(CH_3)COOH$), reaction with dicyanogen or hydrogen sulphide (for example $R^5$: Br→CN, CN→$CSNH_2$), conversion of carboxyl compounds into other carboxylic acid derivatives by customary methods (for example $R^2$: COOH→CN, CN→$CSNH_2$, COOH→$COOCH_3$, $COOCH_3$→$CONH_2$; cf. the preparation examples).

If, for example, 1-(4-cyano-2,5-difluorophenyl)-4-chlorodifluoromethyl-3,6-dihydro-2,6-dioxo-1(2H)-pyrimidine and ethyl 1-(4-hydroxy-phenoxy)-propionate are used as starting materials, the course of the reaction in process (a) according to the invention can be outlined by the following formula scheme:

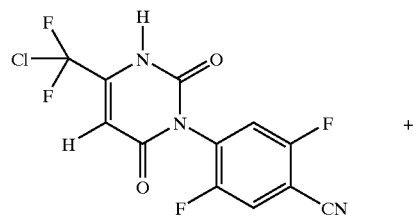

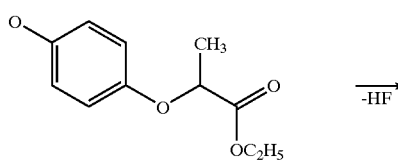

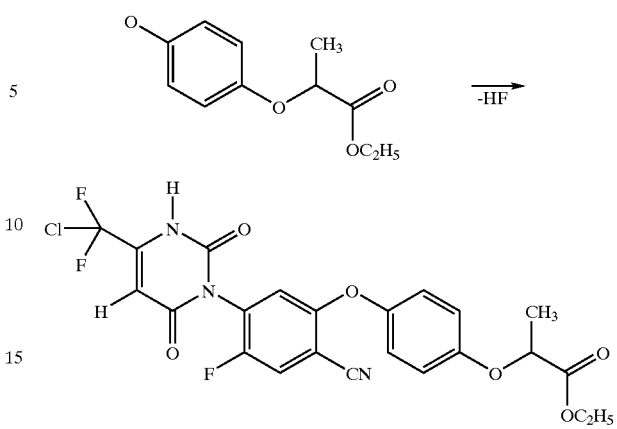

If, for example, methyl 3-amino-4,4,4-trifluoro-crotonate and 4-cyano-2-fluoro-5-phenoxy-phenyl isocyanate are used as starting materials, the course of the reaction in process (b) according to the invention can be outlined by the following formula scheme:

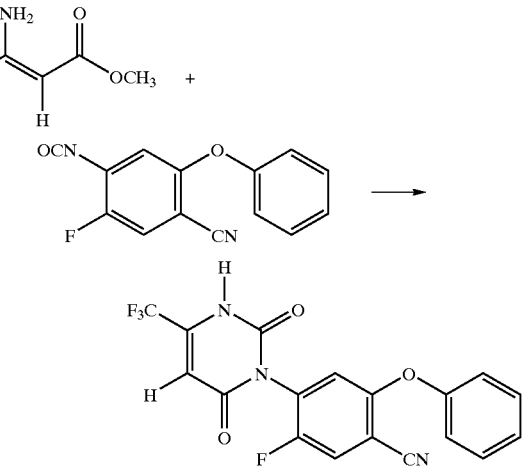

If, for example, methyl [1-(2,4-dichloro-5-phenylthiophenyl)-2,5-dioxo-2,5-dihydro-1H-pyrrol-3-yl]-carbamate is used as starting material, the course of the reaction in the process according to the invention can be outlined by the following formula scheme:

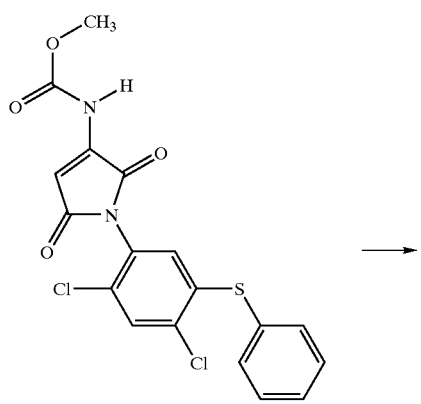

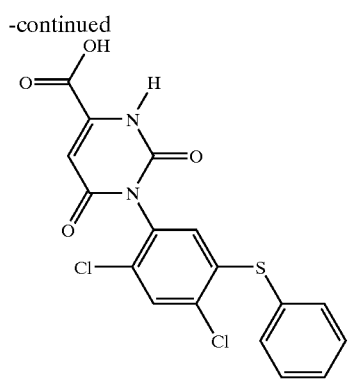

If, for example, 1-[2-chloro-4-trifluoromethyl-5-(4-methoxycarbonylmethoxy-phenoxy)phenyl]-4-difluoromethyl-3,6-dihydro-2,6-dioxo-1(2H)-pyrimidine and methyl bromide are used as starting materials, the course of the reaction in process (d) according to the invention can be outlined by the following formula scheme:

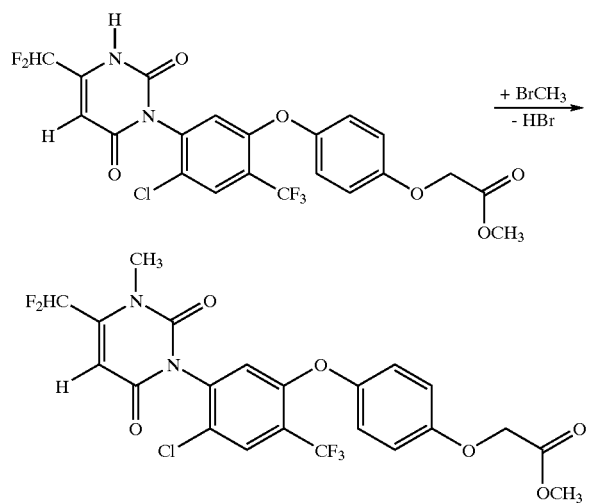

Formula (II) provides a general definition of the halogenophenyluracils to be used as starting materials in process (a) according to the invention for the preparation of compounds of the formula (I). In formula (II), $R^1$, $R^2$, $R^3$, $R^4$ and $R^5$ have, in particular, those meanings which have already been mentioned above in connection with the description of the compounds of the formula (I) according to the invention as being preferred, especially preferred or very especially preferred for $R^1$, $R^2$, $R^3$, $R^4$ and $R^5$; $X^1$ is preferably fluorine or chlorine, in particular fluorine.

The starting materials of the general formula (II) are known and/or can be prepared by processes known per se (cf. EP-A-648749).

Formula (III) provides a general definition of the aryl compounds also to be used as starting materials in process (a) according to the invention. In formula (III) n, Q and X have, in particular, those meanings which have already been mentioned above in connection with the description of the compounds of the formula (I) according to the invention as being preferred, especially preferred or very especially preferred for n, Q and X.

The starting materials of the general formula (III) are known chemicals for organic synthesis.

Formula (IV) provides a general definition of the aminoalkenoic esters to be used as starting materials in process (b) according to the invention for the preparation of compounds of the general formula (I). In the general formula (IV), $R^2$ and $R^3$ have, in particular, those meanings which have already been mentioned above in connection with the description of the compounds of the general formula (I) according to the invention as being preferred, especially preferred or very especially preferred for $R^2$ and $R^3$; R preferably represents $C_1$–$C_4$-alkyl, phenyl or benzyl, in particular methyl or ethyl.

The starting materials of the general formula (IV) are known and/or can be prepared by processes known per se (cf. J. Heterocycl. Chem. 9 (1972), 513–522).

Formula (V) provides a general definition of the aryl isocyanates also to be used as starting materials in process (b) according to the invention. In the general formula (V), n, Q, $R^4$, $R^5$ and X have, in particular, those meanings which have already been mentioned above in connection with the description of the compounds of the general formula (I) according to the invention as being preferred, especially preferred or very especially preferred for n, Q, $R^4$, $R^5$ and X.

The starting materials of the general formula (V) were hitherto unknown from the literature; being new substances, they are also subject-matter of the present application.

The new aryl isocyanates of the general formula (V) are obtained when aniline derivatives of the general formula (IX)

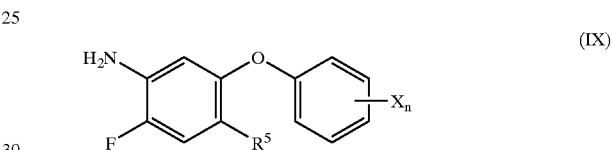

in which n, Q, $R^4$, R5 and X have the abovementioned meaning are reacted with phosgene in the presence of a diluent such as, for example, chlorobenzene, at temperatures between −20° C. and +150° C. (cf., for example, also EP-A-648749).

Formula (VI) provides a general definition of the arylurethanes optionally to be used as starting materials in process (b) according to the invention. In the general formula (VI), n, Q, $R^4$, $R^5$ and X have, in particular, those meanings which have already been mentioned above in connection with the description of the compounds of the general formula (I) according to the invention as being preferred, especially preferred or very especially preferred for n, Q, $R^4$, $R^5$ and X; R preferably represents $C_1$–$C_4$-alkyl, phenyl or benzyl, in particular methyl or ethyl.

The starting materials of the general formula (VI) were hitherto unknown from the literature; being new substances, they are also subject-matter of the present application.

The new arylurethanes of the general formula (VI) are obtained when aniline derivatives of the general formula (IX)

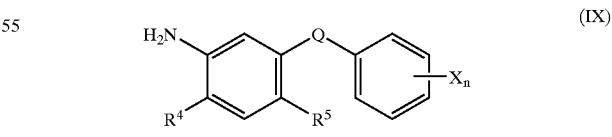

in which n, Q, $R^4$, $R^5$ and X have the abovementioned meaning are reacted with chlorocarbonyl compounds of the general formula (X)

in which
R has the abovementioned meaning,
if appropriate in the presence of an acid acceptor such as, for example, pyridine, and, if appropriate, in the presence of a diluent such as, for example, methylene chloride, at temperatures between −20° C. and +100° C. (cf. the preparation examples).

The aniline derivatives of the general formula (IX) which are required as precursors are known and/or can be prepared by processes known per se (cf. Justus Liebigs Ann. Chem. 740 (1970), 169–179; U.S. Pat. Nos. 3,715,395; 3,914,418; DE-A-2,748,554; DE3,736,089).

The aniline derivatives of the general formula ((IXa)

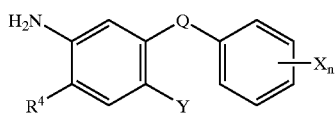

(IXa)

in which
n, R$^4$ and X have the abovementioned meaning and
Y represents cyano, thiocarbamoyl or trifluoromethyl
were hitherto unknown and, being new substances, are subject-matter of the present application.

The new aniline derivatives of the general formula (IXa) are obtained when anilines of the general formula (XI)

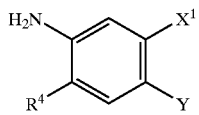

(XI)

in which
R$^4$, X$^1$ and Y have the abovementioned meaning
are reacted with aryl compounds of the general formula (III)

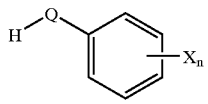

(III)

in which
n, Q and X have the abovementioned meaning
or with metal salts of compounds of the general formula (III),
if appropriate in the presence of a reaction auxiliary such as, for example, sodium hydride and, if appropriate, in the presence of a diluent such as, for example, N-methylpyrrolidone at temperatures between 0° C. and 150° C. (cf. the preparation examples).

Formula (VII) provides a general definition of the N-aryl-1-alkoxy-carbonylamino-maleimides to be used as starting materials in process (c) according to the invention for the preparation of compounds of the general formula (I). In the general formula (VII), n, Q, R$^3$, R$^4$, R$^5$ and X have, in particular, those meanings which have already been mentioned above in connection with the description of the compounds of the general formula (I) according to the invention as being preferred, especially preferred or very especially preferred for n, Q, R$^3$, R$^4$, R$^5$ and X; R' preferably represents C$_1$–C$_4$-alkyl, in particular methyl or ethyl.

The new N-aryl-1-alkoxycarbonylamino-maleimides of the general formula (VII) are obtained when alkyl (2,5-dioxo-2,5-dihydro-furan-3-yl)-carbamates of the general formula (XII)

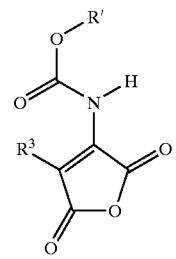

(XII)

in which
R$^3$ has the abovementioned meaning and
R' represents alkyl (in particular methyl or ethyl)
are reacted with aniline derivatives of the general formula (IX)

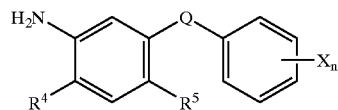

(IX)

in which
n, Q, R$^4$, R$^5$ and X have the abovementioned meaning,
if appropriate in the presence of a diluent such as, for example, acetic acid at temperatures between 0° C. and 200° C., preferably between 50° C. and 150° C.

The precursors of the general formula (XII) are known and/or can be prepared by processes known per se (cf. DE 19604229).

Formula (Ia) provides a general definition of the substituted phenyluracils to be used as starting materials in process (d) according to the invention for the preparation of compounds of the formula (I). In formula (Ia), n, Q, R$^2$, R$^3$, R$^4$, R$^5$ and X have, in particular, those meanings which have already been mentioned above in connection with the description of the compounds of the formula (I) according to the invention as being preferred, especially preferred or very especially preferred for n, Q, R$^2$, R$^3$, R$^4$, R$^5$ and X.

Being new substances, the starting materials of the general formula (Ia) for process (b) are also subject-matter of the present application; they can be prepared by processes (a), (b) and (c) according to the invention.

Formula (VIII) provides a general definition of the alkylating agents also to be used as starting materials in process (d) according to the invention. In formula (VIII), A$^1$ preferably represents alkyl which has 1 to 4 carbon atoms and which is optionally substituted by cyano, halogen or C$_1$–C$_4$-alkoxy and X$^2$ preferably represents chlorine, bromine, iodine, methylsulphonyloxy or ethylsulphonyloxy; in particular, A$^1$ represents methyl, ethyl, n- or i-propyl, each of which is optionally substituted by cyano, fluorine, chlorine, methoxy or ethoxy, and X$^2$ represents chlorine, bromine, iodine, methylsulphonyloxy or ethylsulphonyloxy.

The starting materials of the formula (VIII) are known chemicals for organic synthesis.

The processes according to the invention for the preparation of the compounds of the general formula (I) are preferably carried out using diluents. Suitable diluents for carrying out processes (a), (b), (c) and (d) according to the invention are, besides water, mainly inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, dilsopropyl ether, dioxane, tetrahydrofuran or ethylene glycol dimethyl ether or ethylene glycol diethyl ether, ketones such as acetone, butanone or methyl isobutyl ketone; nitriles such as acetonitrile, propionitrile or butyronitrile; amides such as N,N-dimethylformarnide, N,N-dimethylacetamide, N-methylformanilide, N-methylpyrrolidone or hexamethylphosphoric triamide; esters such as methyl acetate or ethyl acetate, sulphoxides such as dimethyl sulphoxide, alcohols such as methanol, ethanol, n- or i-propanol, ethylene glycol monomethyl ether, ethylene glycol monoethyl ether, diethylene glycol monomethyl ether, diethylene glycol monoethyl ether, mixtures of these with water, or pure water.

Suitable reactants for processes (a), (b), (c) and (d) according to the invention are, generally, the customary inorganic or organic bases or acid acceptors. These preferably include the acetates, amides, carbonates, hydrogencarbonates, hydrides, hydroxides or alkoxides of alkali metals or alkaline earth metals such as, for example, sodium acetate, potassium acetate, calcium acetate, lithium amide, sodium amide, potassium amide, calcium amide, sodium carbonate, potassium carbonate, calcium carbonate, sodium hydrogencarbonate, potassium hydrogencarbonate, calcium hydrogencarbonate, lithium hydride, sodium hydride, potassium hydride, calcium hydride, lithium hydroxide, sodium hydroxide, potassium hydroxide, calcium hydroxide, sodium methoxide, sodium ethoxide, sodium n- or i-propoxide, sodium n-, i-, s- or t-butoxide, potassium methoxide, potassium ethoxide, potassium n- or i-propoxide, or potassium n-, i-, s- or t-butoxide; furthermore also basic organic nitrogen compounds such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2,2,2]-octane (DABCO), 1,5-diazabicyclo[4,3,0]-non-5-en (DBN), or 1,8-diazabicyclo[5,4,0]-undec-7-en (DBU).

Other suitable reactants for the processes according to the invention are phase transfer catalysts. Examples of such catalysts which may be mentioned are:

Tetrabutylammonium bromide, tetrabutylammonium chloride, tetraoctylammonium chloride, tetrabutylammonium hydrogen sulphate, methyltrioctylammonium chloride, hexadecyltrimethylammonium chloride, hexadecyltrimethylammonium bromide, benzyltrimethylammonium chloride, benzyltriethylammonium chloride, benzyltrimethylammonium hydroxide, benzyltriethylammonium hydroxide, benzyltributylammonium chloride, benzyltributylammonium bromide, tetrabutylphosphonium bromide, tetrabutylphosphonium chloride, tributylhexadecylphosphonium bromide, butyltriphenylphosphonium chloride, ethyltrioctylphosphonium bromide, tetraphenylphosphonium bromide.

When carrying out processes (a), (b), (c) and (d) according to the invention, the reaction temperatures can be varied within a substantial range. In general, the process is carried out at temperatures between 0° C. and 150° C., preferably between 10° C. and 120° C.

The processes according to the invention are generally carried out under atmospheric pressure. However, it is also possible to carry out the processes according to the invention under elevated or reduced pressure, in general between 0.1 bar and 10 bar.

To carry out the processes according to the invention, the starting materials are generally employed in approximately equimolar amounts. However, it is also possible to use one of the components in a larger excess. In general, the reaction is carried out in a suitable diluent in the presence of a reaction auxiliary, and the reaction mixture is generally stirred for several hours at the temperature required. Working-up is by customary methods (cf. the preparation examples).

The active compounds according to the invention can be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used. The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds of the formula (I) according to the invention show a potent herbicidal activity and a broad spectrum of action when applied to the soil and to aerial parts of plants. To some extent, they are also suitable for the selective control of monokotyledonous and dikotyledonous weeds in monokotyledonous and dikotyledonous crops, both by the pre- and the post-emergence method.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolyzates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, ready-mixes or tank mixes being possible.

Possible components for the mixtures are known herbicides, such as, for example, acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzofenap, benzoylprop (-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlonitrofen, chlorsulfuron, chlortoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, di-allate, dicamba, diclofop(-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymrone, epoprodan, EPTC, esprocarb, ethalfluralin, ethametsulfuron(-methyl), ethofumesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen (-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazametha-benz(-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop (-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, tri-allate, triasulfuron, tribenuron(-methyl), triclopyr, tridiphane, trifluralin and triflusulfuron.

Mixtures with other known active compounds such as fungicides, insecticides, acaricides, nematicides, bird repellants, plant nutrients and soil conditioners, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by pouring, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the application rates are between 1 and 10 kg of active compound per hectare of soil surface, preferably between 5 and 5 kg per ha.

The preparation and use of the active compounds according to the invention can be seen from the examples which follow.

PREPARATION EXAMPLES

Example 1

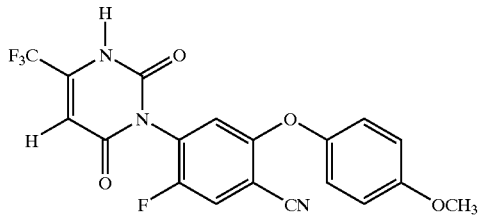

(Process (a))

2.5 g (10 mmol) of 4-methoxy-phenol in 50 ml. of dimethyl sulphoxide are treated with 1.6 g of sodium hydride (purity 60%). The mixture is stirred for 30 minutes at room temperature (approx. 20° C.). Then, 3.2 g (10 mmol) of 4-(3,6-dihydro-2,6-dioxo-4-trifluoromethyl-1(2H)-pyrimidin-1-yl)-2,5-difluorobenzonitrile are added. The reaction mixture is stirred for 18 hours at 60° C. and subsequently poured into approximately an equal volume of 1N hydrochloric acid. The product, which is obtained as crystals, is isolated by filtration with suction, stirred with a mixture of 30 ml of ethyl acetate and 300 ml of diethyl ether and filtered with suction to dryness. The organic mother liquor is concentrated under a water pump vacuum and the residue is processed by column chromatography (silica gel, chloroform/ethyl acetate, vol.: 2:1). The first fraction obtained is concentrated under a water pump vacuum, and the residue is dissolved in boiling methylene chloride; when cold, the supernatant solvent is decanted off, the residue is stirred with diethyl ether/diisopropyl ether, and the crystalline product is isolated by filtration with suction.

This gives 0.90 g (21% of theory) of 4-(3,6-dihydro-2,6-dioxo-4-trifluoromethyl-1(2H)-pyrimidin-1-yl)-5-fluoro-2-(4-methoxy-phenoxy)-benzonitrile of melting point 84° C.

Example 2

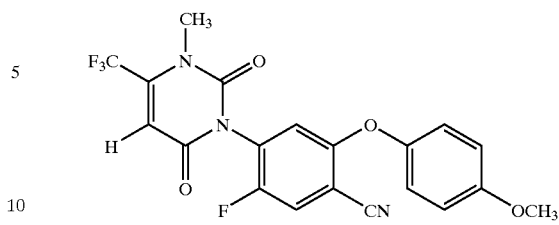

(Process (b))

A mixture of 0.50 g (1.2 mmol) of 4-(3,6-dihydro-2,6-dioxo-4-trifluoromethyl-1(2H)-pyrimidin-1-yl)-5-fluoro-2-(4-methoxy-phenoxy)-benzonitrile, 0.20 g (1.8 mmol) of dimethyl sulphate, 0.30 g (2.4 mmol) of potassium carbonate and 100 ml of acetone is refluxed for 15 hours and subsequently concentrated under a water pump vacuum. The residue is shaken with 50 ml of 1N hydrochloric acid/50 ml of ethyl acetate, and the organic phase is separated off, dried with sodium sulphate and filtered. The filtrate is concentrated under a water pump vacuum, the residue is dissolved in ethyl acetate, and the solution is washed with 5% aqueous disodium hydrogen phosphate solution, dried with sodium sulphate and filtered. The filtrate is concentrated under a water pump vacuum, the residue is stirred with petroleum ether, and the solvent is carefully distilled off under a water pump vacuum.

This gives 0.3 g (57% of theory) of 4-(3,6-dihydro-2,6-dioxo-3-methyl-4-trifluoromethyl-1(2H)-pyrimidin-1-yl)-5-fluoro-2-(4-methoxy-phenoxy)-benzonitrile of melting point 62° C.

Other examples of the compounds of the formula (I) which can be prepared analogously to Preparation Examples 1 and 2 and following the general description of the preparation processes according to the invention are those listed in Table 1 which follows.

TABLE 1

Examples of the compounds of the formula (I)

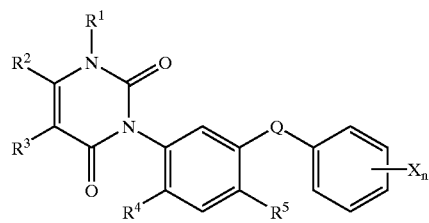

| Ex. No. | n | Q | $R^1$ | $R^2$ | $R^3$ | $R^4$ | $R^5$ | (Position-) X | Physical data and stereochemical details |
|---|---|---|---|---|---|---|---|---|---|
| 3 | 1 | O | H | $CF_3$ | H | F | CN | (4-) 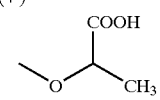 | (R enantiomer) |
| 4 | 1 | O | $CH_3$ | $CF_3$ | H | F | CN | (4-) 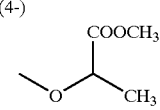 | m.p.: 118° C. (R enantiomer) |

TABLE 1-continued

Examples of the compounds of the formula (I)

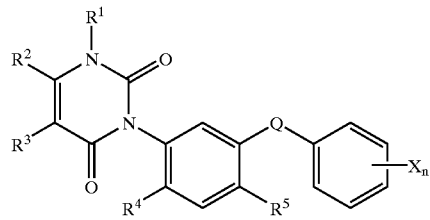

| Ex. No. | n | Q | R¹ | R² | R³ | R⁴ | R⁵ | (Position-) X | | Physical data and stereo-chemical details |
|---|---|---|---|---|---|---|---|---|---|---|
| 5 | 1 | O | H | $CF_3$ | H | F | CN | (4-) | 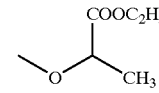 | m.p.: 105° C. (R enantiomer) |
| 6 | 1 | O | $CH_3$ | $CF_3$ | H | F | CN | (4-) | 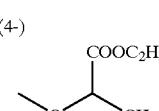 | m.p.: 146° C. (R enantiomer) |
| 7 | 1 | O | $NH_2$ | $CF_3$ | H | F | CN | (4-) | 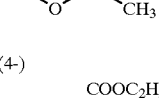 | m.p.: 152° C. (R enantiomer) |
| 8 | 1 | O | H | $CF_3$ | H | F | CN | (4-) | 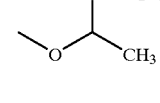 | $^1$H NMR: δ = 6.42 ppm (s, $D_6$-DMSO) |
| 9 | 1 | O | H | $CF_3$ | H | F | 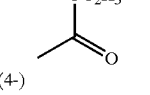 | (4-) $OCH_3$ | | $^1$H NMR: δ = 5.63 ppm (s, $D_6$-DMSO) |
| 10 | 1 | O | H | $CF_3$ | H | F | CN | (4-) | 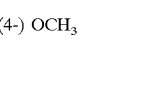 | m.p.: 95° C. (R enantiomer) |
| 11 | 1 | O | $CH_3$ | $CF_3$ | H | F |  | (4-) | 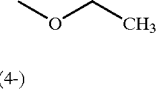 | $^1$H NMR: δ = 6.51 ppm (s, $D_6$-DMSO) (R enantiomer) |
| 12 | 1 | O | $CH_3$ | $CF_3$ | H | F | CN | (4-) | 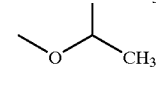 | m.p.: 155° C. |
| 13 | 1 | O | $CH_3$ | $CF_3$ | H | F | CN | (4-) |  | m.p.: 98° C. (E isomer) |

TABLE 1-continued
Examples of the compounds of the formula (I)
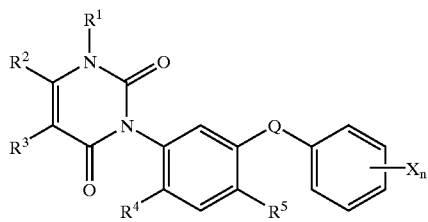
| Ex. No. | n | Q | $R^1$ | $R^2$ | $R^3$ | $R^4$ | $R^5$ | (Position-) X | Physical data and stereochemical details |
|---|---|---|---|---|---|---|---|---|---|
| 14 | 1 | O | $CH_3$ | $CF_3$ | H | F | CN | (4-) 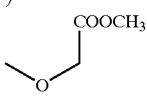 | m.p.: 144° C. (R enantiomer) |
| 15 | 0 | O | $CH_3$ | $CF_3$ | H | F | CN | — | |
| 16 | 1 | O | $CH_3$ | $CF_3$ | H | F | CN | (2-) F | |
| 17 | 1 | O | $CH_3$ | $CF_3$ | H | F | CN | (4-) 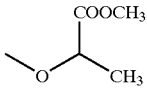 | |
| 18 | 1 | O | $CH_3$ | $CF_3$ | H | F | CN | (3-) 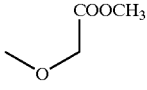 | |
| 19 | 1 | O | $CH_3$ | $CF_3$ | H | F | CN | (3-) 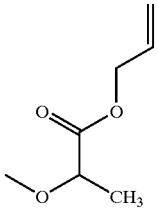 | |
| 20 | 2 | O | $CH_3$ | $CF_3$ | H | F | CN | (2,4-) $Cl_2$ | |
| 21 | 1 | O | H | $CF_3$ | H | F | CN | (4-) 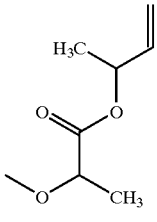 | m.p.: 173° C. (R enantiomer) |
| 22 | 1 | O | H | $CF_3$ | H | F | CN | (4-)  | m.p.: 148° C. (R enantiomer) |
| 23 | 1 | O | H | $CF_3$ | H | F | CN | (4-) OH | m.p.: 191° C. |

TABLE 1-continued

Examples of the compounds of the formula (I)

| Ex. No. | n | Q | $R^1$ | $R^2$ | $R^3$ | $R^4$ | $R^5$ | (Position-) X | Physical data and stereo-chemical details |
|---|---|---|---|---|---|---|---|---|---|
| 24 | 1 | O | $CH_3$ | $CF_3$ | H | F | CN | (4-) [allyl 2-methoxypropanoate group] | m.p.: 126° C. (R enantiomer) |
| 25 | 1 | O | $CH_3$ | $CF_3$ | H | F | CN | (4-) OH | $^1$H NMR (D6-DMSO, δ): 6.54 ppm |
| 26 | 1 | O | H | $CF_3$ | H | F | CN | (4-) [benzyl 2-methoxypropanoate group] | m.p.: 64° C. (R enantiomer) |
| 27 | 1 | O | $CH_3$ | $CF_3$ | H | F | CN | (4-) [benzyl 2-methoxypropanoate group] | m.p.: 75° C. (R enantiomer) |
| 28 | 1 | O | $CH_3$ | $CF_3$ | H | F | CN | (4-) [ethyl 2-methoxypropanoate group] | $^1$H NMR ($CDCl_3$, δ): 3.5 ppm (racemate) |
| 29 | 1 | O | $CH_3$ | $CF_3$ | H | F | CN | (4-) [ethyl 2-methoxypropanoate group] | m.p.: 140° C. (racemate) |
| 30 | 1 | O | $CH_3$ | $CF_3$ | H | F | CN | (4-) [2-methoxypropanoic acid group] | (R enantiomer) |

TABLE 1-continued

Examples of the compounds of the formula (I)

[Structure: pyrimidine-2,4-dione with R¹ on N, R² and R³ on the C=C, linked via N to a phenyl ring bearing R⁴, R⁵, and an O-phenyl group substituted with Xₙ]

| Ex. No. | n | Q | R¹ | R² | R³ | R⁴ | R⁵ | (Position-) X | Physical data and stereochemical details |
|---|---|---|---|---|---|---|---|---|---|
| 31 | 1 | O | $CH_3$ | $CF_3$ | H | F | CN | (4-) —CH(OCH₃)C(O)NH(CH₃) | (R enantiomer) |
| 32 | 1 | O | $CH_3$ | $CF_3$ | H | F | CN | (4-) —CH(OCH₃)C(O)N(CH₃)₂ | (R enantiomer) |
| 33 | 1 | O | $CH_3$ | $CF_3$ | H | F | CN | (4-) —CH(OCH₃)C(O)NH(C₆H₅) | (R enantiomer) |
| 34 | 1 | O | $CH_3$ | $CF_3$ | H | F | CN | (4-) —CH(OCH₃)C(O)NH(CH₂C₆H₅) | (R enantiomer) |
| 35 | 1 | O | $CH_3$ | $CF_3$ | H | F | C(=S)NH₂ | (4-) —CH(OCH₃)C(O)NH(CH₃) | (R enantiomer) |
| 36 | 1 | O | $CH_3$ | $CF_3$ | H | F | C(=S)NH₂ | (4-) —CH(OCH₃)C(O)N(CH₃)₂ | (R enantiomer) |
| 37 | 0 | S | $CH_3$ | $CF_3$ | H | F | CN | — | |

TABLE 1-continued

Examples of the compounds of the formula (I)

| Ex. No. | n | Q | R¹ | R² | R³ | R⁴ | R⁵ | (Position-) X | Physical data and stereochemical details |
|---|---|---|---|---|---|---|---|---|---|
| 38 | 1 | O | NH₂ | CF₃ | H | F | CN | (4-) -C(=O)-O-C₂H₅ (acetate ester with OC₂H₅) | |
| 39 | 1 | O | CH₃ | CF₃ | H | F | CN | (4-) O-CH(CH₃)-C(=O)-O-CH(CH₃)-C≡CH (methoxy-propanoate with but-3-yn-2-yl) | (R enantiomer) |
| 40 | 1 | O | CH₃ | CF₃ | H | F | C(=S)NH₂ | (4-) O-CH(CH₃)-COOC₂H₅ | (R enantiomer) |
| 41 | 1 | O | CH₃ | CF₃ | H | F | CN | (2-) OCH₃ | |
| 42 | 1 | O | CH₃ | CF₃ | H | F | C(=S)NH₂ | (2-) OCH₃ | |
| 43 | 1 | O | CH₃ | CF₃ | H | F | CN | (3-) OCH₃ | m.p.: 140° C. |
| 44 | 1 | O | CH₃ | CF₃ | H | F | C(=S)NH₂ | (3-) OCH₃ | |
| 45 | 1 | O | CH₃ | CF₃ | H | F | CN | (2-) OH | |
| 46 | 1 | O | CH₃ | CF₃ | H | F | C(=S)NH₂ | (2-) OH | |
| 47 | 1 | O | CH₃ | CF₃ | H | F | CN | (3-) OH | |
| 48 | 1 | O | CH₃ | CF₃ | H | F | C(=S)NH₂ | (3-) OH | |
| 49 | 1 | O | CH₃ | CF₃ | H | F | C(=S)NH₂ | (4-) OH | |
| 50 | 1 | O | CH₃ | CF₃ | H | F | CN | (4-) SCH₃ | |

TABLE 1-continued

Examples of the compounds of the formula (I)

| Ex. No. | n | Q | R¹ | R² | R³ | R⁴ | R⁵ | (Position-) X | Physical data and stereochemical details |
|---|---|---|---|---|---|---|---|---|---|
| 51 | 1 | O | $CH_3$ | $CF_3$ | H | F | $\underset{S}{\overset{NH_2}{\diagdown}}\!\!\!\diagup$ | (4-) $SCH_3$ | |
| 52 | 1 | O | $CH_3$ | $CF_3$ | H | F | CN | (4-) SH | |
| 53 | 1 | O | $CH_3$ | $CF_3$ | H | F | CN | $-O-CH_2-O-C(O)-CH_3$ (4) | m.p.: 83° C. |
| 54 | 1 | O | $CH_3$ | $CF_3$ | H | F | CN | $-O-CH_2-O-C(O)-C_6H_5$ (4) | |
| 55 | 1 | O | $CH_3$ | $CF_3$ | H | F | CN | $-O-CH_2-O-C(O)-NH-CH_3$ (4) | m.p.: 147° C. |
| 56 | 1 | O | $CH_3$ | $CF_3$ | H | F | CN | (4-) $-O-CH_2-COOH$ | |
| 57 | 1 | O | $CH_3$ | $CF_3$ | H | F | CN | (4-) $-O-CH_2-COOC_2H_5$ | m.p.: 156° C. |
| 58 | 1 | S | $CH_3$ | $CF_3$ | H | F | CN | (2-) OH | |
| 59 | 1 | S | $CH_3$ | $CF_3$ | H | F | CN | (3-) OH | |
| 60 | 1 | S | $CH_3$ | $CF_3$ | H | F | CN | (4-) OH | |
| 61 | 1 | O | $CH_3$ | $CF_3$ | H | F | CN | (2-) $NO_2$ | |
| 62 | 1 | O | $CH_3$ | $CF_3$ | H | F | CN | (3-) $NO_2$ | |
| 63 | 1 | O | $CH_3$ | $CF_3$ | H | F | CN | (4-) $NO_2$ | |
| 64 | 1 | O | $CH_3$ | $CF_3$ | H | F | CN | (2-) $NH_2$ | |
| 65 | 1 | O | $CH_3$ | $CF_3$ | H | F | CN | (3-) $NH_2$ | |
| 66 | 1 | O | $CH_3$ | $CF_3$ | H | F | CN | (4-) $NH_2$ | |
| 67 | 2 | O | $CH_3$ | $CF_3$ | H | F | CN | (3,5-) $Cl_2$ | |
| 68 | 1 | S | $CH_3$ | $CF_3$ | H | F | CN | (4-) Cl | |
| 69 | 1 | O | $CH_3$ | $CF_3$ | H | F | CN | (4-) $CH_3$ | |
| 70 | 1 | S | $CH_3$ | $CF_3$ | H | F | CN | (4-) $CH_3$ | |

TABLE 1-continued

Examples of the compounds of the formula (I)

| Ex. No. | n | Q | R¹ | R² | R³ | R⁴ | R⁵ | (Position-) X | Physical data and stereo-chemical details |
|---|---|---|---|---|---|---|---|---|---|
| 71 | 1 | O | H | -C(OH)(-)C(=O)- (acetyl with OH) | H | F | CN | (4-) OCH$_3$ | |
| 72 | 1 | O | CH$_3$ | -C(OCH$_3$)(-)C(=O)- | H | F | CN | (4-) OCH$_3$ | |
| 73 | 1 | O | CH$_3$ | -C(NH$_2$)(-)C(=O)- | H | F | CN | (4-) OCH$_3$ | log P = 1.92[a] |
| 74 | 1 | O | CH$_3$ | CN | H | F | CN | (4-) OCH$_3$ | m.p.: 174° C. log P = 2.69[a] |
| 75 | 1 | O | CH$_3$ | -C(NH$_2$)=S | H | F | -C(NH$_2$)=S | (4-) OCH$_3$ | |
| 76 | 1 | O | CH$_3$ | CN | H | F | CN | (4-) OH | |
| 77 | 1 | O | CH$_3$ | CN | H | F | CN | (4-) -O-CH(CH$_3$)-COOH | (R enantiomer) |
| 78 | 1 | O | CH$_3$ | CN | H | F | CN | (4-) -O-CH(CH$_3$)-COOH | (R enantiomer) |
| 79 | 1 | O | CH$_3$ | CN | H | F | CN | (4-) -O-CH(CH$_3$)-C(=O)-NH-CH$_3$ | (R enantiomer) |
| 80 | 1 | O | CH$_3$ | -C(NH$_2$)=S | H | F | -C(NH$_2$)=S | (4-) -O-CH(CH$_3$)-COOCH$_3$ | (R enantiomer) |

TABLE 1-continued

Examples of the compounds of the formula (I)

| Ex. No. | n | Q | R¹ | R² | R³ | R⁴ | R⁵ | (Position-) X | Physical data and stereo-chemical details |
|---|---|---|---|---|---|---|---|---|---|
| 81 | 1 | O | CH₃ | CF₃ | H | F | CN | (4-) <br> *(structure: –CH₂–O–C(=O)–N(CH₃)₂)* | (amorphous) |
| 82 | 1 | O | CH₃ | CF₃ | H | F | CN | (4-) <br> *(structure: –CH(CH₃)–O–CH(CH₃)–COOC₃H₇-n)* | m.p.: 130° C. (racemate) |

Starting Materials of the Formula (VI)

Example (VI-1)

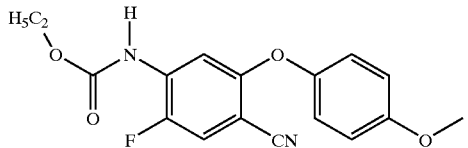

2.8 g (11 mmol) 1-amino-4-cyano-2-fluoro-5-(4-methoxy-phenoxy)benzene in 100 ml of methylene chloride and 1.7 g of pyridine are treated at room temperature (approx. 20° C.) with 1.25 g (12 mmol) of ethyl chloroformate. The mixture is stirred for 2 hours at room temperature and subsequently shaken with 1N hydrochloric acid. The organic phase is concentrated under a water pump vacuum, the residue is crystallized from diethyl ether/diisopropyl ether, and the solid product is isolated by filtration with suction.

This gives 1.2 g (34% of theory) of O-ethyl N-(4-cyano-2-fluoro-5-(4-methoxy-phenoxy)-phenyl-carbamate.

$^1$H NMR (D6-DMSO, δ): 7.85 and 7.89 ppm.

Starting Materials of the Formula (IX)

Example (IX-1)

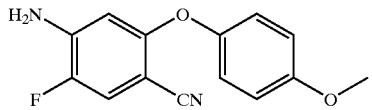

1.3 g (10 mmol) of 4-methoxy-phenol in 100 ml N-methyl-pyrrolidone are treated at room temperature with 0.50 g of sodium hydride (purity 60%) and, after brief stirring, with 1.5 g of 4-cyano-2,5-difluoro-aniline. The reaction mixture is then stirred for 20 hours at 100° C. When cold, the mixture is diluted with water and then with 1N-hydrochloric acid and, after stirring for two hours, the solid product is isolated by filtration with suction and dried on clay.

This gives 1.9 g (73% of theory) of 1-amino-4-cyano-2-fluoro-5-(4-methoxy-phenoxy)-benzene of melting point 135° C.

Other compounds of the general formula (IX) which can be prepared analogously to Example (IX-1) are those listed in Table 2 which follows.

TABLE 2

Examples of the compounds of the formula (IX)

(IX)

| Ex.-No. | Q | R⁴ | R⁵ | X_n | Physical data |
|---|---|---|---|---|---|
| IX-2 | O | F | CN | (3-) OCH₃ | m.p.: 94° C. |
| IX-3 | O | F | CN | (2-) OCH₃ | |
| IX-4 | O | F | CN | (4-) Cl | |
| IX-5 | O | F | CN | (3-) Cl | |
| IX-6 | O | F | CN | (2-) Cl | |
| IX-7 | O | F | CN | (4-) OH | |

TABLE 2-continued

Examples of the compounds of the formula (IX)

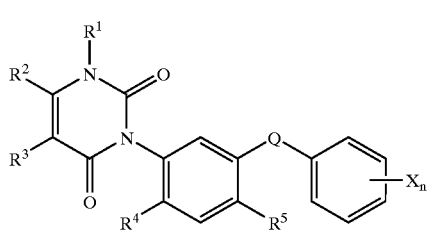

| Ex.-No. | Q | R⁴ | R⁵ | Xₙ | Physical data |
|---|---|---|---|---|---|
| IX-8 | O | F | CN | (4-) COOCH₃ on OCH(CH₃) | |
| IX-9 | O | F | CN | — | |
| IX-10 | O | F | CN | (4-) F | |
| IX-11 | O | F | CN | (3-) F | |
| IX-12 | O | F | CN | (2-) F | |
| IX-13 | O | F | CN | (4-) Br | |
| IX-14 | O | H | CN | (4-) OH | |
| IX-15 | O | H | CN | (4-) OCH₃ | |
| IX-16 | O | H | CN | (4-) Cl | |
| IX-17 | O | H | CN | (4-) F | |
| IX-18 | O | F | CF₃ | — | |
| IX-19 | O | F | CF₃ | (4-) CH₃ | |
| IX-20 | O | F | CF₃ | (4-) OCH₃ | |
| IX-21 | S | H | CN | — | |
| IX-22 | S | F | CN | — | |
| IX-23 | S | F | CN | (4-) Cl | |
| IX-24 | S | F | CN | (4-) F | |
| IX-25 | O | F | CF₃ | (4-) CN | |

Use Examples

Example A
Pre-emergence Test
Solvent: 5 parts by weight of acetone
Emulsifier: 1 part by weight of alkylaryl polyglycol ether To prepare a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil. After approx. 24 hours, the soil is sprayed with the preparation of active compound in such a way that the desired amount of active compound is applied per unit area. The concentration of the spray mixture is chosen in such a way that the desired amount of active substance is applied in 1000 liters of water per hectare.

After spraying for three weeks, the degree of damage to the plants is scored in % damage in comparison with the development of the untreated control.

The figures denote:

0%=no action (like untreated control)

100%=total destruction

In this test, a potent action against weeds is shown, for example, by the compounds of Preparation Examples 4 and 6.

Example B
Post-emergence Test
Solvent: 5 parts by weight of acetone
Emulsifier 1 part by weight of alkylaryl polyglycol ether To prepare a suitable preparation of active compound, 1 part by weight of active compound is mixed with the stated amount of solvent, the stated amount of emulsifier is added, and the concentrate is diluted with water to the desired concentration.

Test plants which have a height of 5–15 cm are sprayed with the preparation of active compound in such a way that the desired amounts of active compound are applied per unit area. The concentration of the spray mixture is chosen in such a way that the desired amounts of active substance are applied in 1000 liters of water per hectare.

After spraying for three weeks, the degree of damage to the plants is scored in % damage in comparison with the development of the untreated control.

The figures denote:

0%=no action (like untreated control)

100%=total destruction

In this test, a potent action against weeds is shown, for example, by the compounds of Preparation Examples 4 and 6.

What is claimed is:

1. A substituted phenyluracil of the formula (I)

(I)

in which n represents the numbers 0, 1, 2, or 3,

Q represents O, S, SO, SO₂, NH or N(C₁–C₄-alkyl),

R¹ represents hydrogen or C₁–C₄-alkyl which is optionally substituted by cyano, carboxyl, fluorine, chlorine, C₁–C₄-alkoxy or C₁–C₄-alkoxy-carbonyl, R² represents carboxyl, cyano, carbamoyl, or thiocarbamoyl or represents C₁–C₄-alkyl or C₁–C₄-alkoxycarbonyl, each of which is optionally substituted by cyano, fluorine, chlorine or C₁–C₄-alkoxy, R³ represents hydrogen, halogen or C₁–C₄-alkyl which is optionally substituted by cyano, carboxyl, fluorine, chlorine, C₁–C₄-alkoxy or C₁–C₄-alkoxy-carbonyl, R⁴ represents hydrogen, cyano, carbamoyl, thiocarbamoyl or halogen, R⁵ represents cyano, carbamoyl, thiocarbamoyl, or halogen or represents C₁–C₄-alkyl or C₁–C₄-alkoxy, each of which is optionally substituted by fluorine and/or chlorine, X represents alkyl, alkoxy, alkylthio, alkylsulphinyl, alkylsulphonyl, alkylamino, dialkylamino, alkylcarbonyl, alkoxycarbonyl, alkyl-aminocarbonyl, dialkylaminocarbonyl, alkylcarbonyloxy, alkoxycarbonyloxy, alkylaminocarbonyloxy, or dialkylaminocarbonyloxy, each of which has 1 to 6 carbon atoms in each alkyl moiety and is substituted in the alkyl moiety by C₁–C₄-alkoxy, C₁–C₄-alkylthio, C₁–C₄-alkylsulphinyl, C₁–C₄-alkylsulphonyl, C₁–C₄-alkyl-carbonyl, C₁–C₄-alkylaminocarbonyl, di-(C₁–C₄-alkyl)amino-carbonyl, phenoxycarbonyl, benzyloxycarbonyl, or phenylaminocarbonyl; or represents phenylcarbonyloxy; or represents alkylcarbonylamino, alkoxy-carbonylamino, or alkylsulphonylamino, each of which has 1 to 6 carbon atoms in the alkyl moiety and is optionally substituted in the alkyl moiety by fluorine, chlorine or bromine; or represents alkenyl, alkenyloxy, alkenyloxy-carbonyl, alkinyl, alkinyloxy or alkinyloxycarbonyl, each of which has up to 6 carbon atoms and is optionally substituted by cyano, carboxyl, fluorine, chlorine, bromine or $C_1$–$C_4$-alkoxy-carbonyl, where, in the event that n is greater than 1, each X is defined independently.

2. A substituted phenyluracil according to claim 1 wherein n represents the numbers 0, 1, 2, or 3, Q represents O, S, SO, $SO_2$, NH or N($C_1$–$C_4$-alkyl), $R^1$ represents hydrogen or $C_1$–$C_4$-alkyl which is optionally substituted by cyano, carboxyl, fluorine, chlorine, $C_1$–$C_4$-alkoxy or $C_1$–$C_4$-alkoxy-carbonyl, $R^2$ represents carboxyl, cyano, carbamoyl, thiocarbamoyl, or represents $C_1$–$C_4$-alkyl or $C_1$–$C_4$-alkoxy-carbonyl, each of which is optionally substituted by cyano, fluorine, chlorine or $C_1$–$C_4$-alkoxy, $R^3$ represents hydrogen, fluorine, chlorine, bromine, or represents $C_1$–$C_4$-alkyl which is optionally substituted by fluorine or chlorine, $R^4$ represents hydrogen, cyano, carbamoyl, thiocarbamoyl, fluorine, chlorine or bromine, $R^5$ represents cyano, carbamoyl, thiocarbamoyl, fluorine, chlorine, bromine, or represents $C_1$–$C_4$-alkyl or $C_1$–$C_4$-alkoxy, each of which is optionally substituted by fluorine and/or chlorine, and X represents alkyl, alkoxy alkylthio, alkylsulphinyl, alkylsulphonyl or alkylamino, each of which has 1 to 6 carbon atoms and each of which is substituted by $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkylaminocarbonyl, di-($C_1$–$C_4$-alkyl)aminocarbonyl, phenoxycarbonyl, benzyloxycarbonyl, phenylaminocarbonyl; or represents dialkylamino having 1 to 6 carbon atoms in each of the alkyl groups; or represents alkylcarbonyl, alkoxycarbonyl, alkylaminocarbonyl, alkylcarbonyloxy, alkoxycarbonyloxy or alkylaminocarbonyloxy, each of which has 1 to 6 carbon atoms in the alkyl groups and each of which is substituted by $C_1$–$C_4$-alkoxy; or represents dialkylaminocarbonyl or dialkylaminocarbonyloxy, each of which has 1 to 6 carbon atoms in the alkyl groups alkyl groups; or represents phenyl-carbonyloxy; or represents alkylcarbonylamino, alkoxycarbonylamino, alkylsulphonylamino, each of which is optionally substituted by fluorine, chlorine or bromine; or represents alkenyl, alkenyloxy, alkenyloxycarbonyl, alkinyl, alkinyloxy or alkinyloxycarbonyl, each of which has up to 6 carbon atoms and each of which is optionally substituted by cyano, carboxyl, fluorine, chlorine, bromine or $C_1$–$C_4$-alkoxy-carbonyl.

3. A substituted phenyluracil according to claim 1 wherein n represents the numbers 1, 2 or 3, Q represents O, S, SO, $SO_2$, NH or N($CH_3$), $R^1$ represents hydrogen or represents methyl, ethyl, n- or i-propyl, each of which is optionally substituted by cyano, fluorine, chlorine, methoxy or thoxy, $R^2$ represents carboxyl, cyano, carbamoyl, thiocarbamoyl, or represents methyl, ethyl, n- or i-propyl, methoxycarbonyl, ethoxycarbonyl, n- or i-propoxycarbonyl, each of which is optionally substituted by cyano, fluorine, chlorine, methoxy or ethoxy, $R^3$ represents hydrogen, fluorine, chlorine, bromine, or represents methyl or ethyl, each of which is optionally substituted by fluorine and/or chlorine, $R^4$ represents hydrogen, fluorine or chlorine, $R^5$ represents cyano, carbamoyl, thiocarbamoyl, fluorine, chlorine, bromine, methyl or trifluoromethyl, and x represents methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethyl-sulphinyl, methylsulphonyl, ethylsulphonyl, methylamino, ethylamino, n- or i-propylamino, n-, i-, s- or t-butylamino, each of which is substituted by methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, n- or i-butyroyl, methylaminocarbonyl, ethylaminocarbonyl, n- or i-propylaminocarbonyl, dimethylaminocarbonyl, diethylaminocarbonyl, phenoxycarbonyl, benzyloxycarbonyl, phenylaminocarbonyl or benzylaminocarbonyl; or represents dimethylamino or diethylamino; or represents acetyl, propionyl, n- or i-butyroyl, methoxycarbonyl, ethoxycarbonyl, n- or i-propoxycarbonyl, methyl-aminocarbonyl, ethylaminocarbonyl, n- or i-propylaminocarbonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, each of which is optionally substituted by cyano, fluorine, chlorine, methoxy, ethoxy, n- or i-propoxy; or represents dimethylaminocarbonyl, diethylaminocarbonyl, dimethylaminocarbonyloxy or diethyl-aminocarbonyloxy, or represents phenylcarbonyloxy, or represents acetyl-amino, propionylamino, n- or i-butyroylamino, methoxycarbonylamino, ethoxy-carbonylamino, n- or i-propoxycarbonylamino, methylsulphonylamino, ethyl-sulphonylamino, n- or i-propylsulphonylamino, n-, i-, s- or t-butylsulphonyl-amino, each of which is optionally substituted by fluorine or chlorine, or represents ethenyl, propenyl, propenyloxy, propenyloxycarbonyl, ethinyl, propinyl, propinyloxy or propinyloxycarbonyl, each of which is optionally substituted by cyano, carboxyl, fluorine, chlorine, methoxycarbonyl or ethoxycarbonyl.

4. A substituted phenyluracil according to claim 1 having the formula (IA)

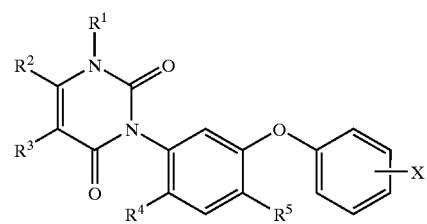

(1A)

in which $R^1$ represents hydrogen or methyl, $R^2$ represents trifluoromethyl, chlorodifluoromethyl, difluoromethyl or pentafluoroethyl, $R^3$ represents hydrogen, chlorine or methyl, $R^4$ represents hydrogen, fluorine or chlorine, $R^5$ represents cyano or thiocarbamoyl, and X represents methyl, ethyl, methoxy, ethoxy, methylthio, ethylthio, methoxycarbonyl or ethoxycarbonyl, each of which is substituted by methoxy, ethoxy, n- or i-propoxy, methyl-aminocarbonyl, ethylaminocarbonyl, n- or i-propylaminocarbonyl, dimethyl-aminocarbonyl, diethylaminocarbonyl, phenoxycarbonyl, benzyloxycarbonyl, phenylaminocarbonyl or benzylaminocarbonyl; or represents ethenyl which is substituted by methoxycarbonyl or ethoxycarbonyl.

5. A substituted phenyluracil according to claim 4 wherein $R^1$ represents methyl, $R^2$ represents trifluoromethyl, chlorodifluoromethyl, difluoromethyl or pentafluoroethyl, $R^3$ represents hydrogen, chlorine or methyl, $R^4$ represents hydrogen, fluorine or chlorine, $R^5$ represents fluorine, chlorine, bromine or trifluoromethyl, and X represents methyl, ethyl, methoxy, ethoxy, methylthio, ethylthio, methoxycarbonyl or ethoxycarbonyl, each of which is substituted by methoxy, ethoxy, n- or i-propoxy, methyl-aminocarbonyl, ethylaminocarbonyl, n- or i-propylaminocarbonyl, dimethyl-aminocarbonyl, diethylaminocarbonyl, phenoxycarbonyl, benzyloxycarbonyl, phenylaminocarbonyl or benzylaminocarbonyl; or represents ethenyl which is substituted by methoxycarbonyl or ethoxycarbonyl.

6. A substituted phenyluracil according to claim 4 wherein $R^1$ represents hydrogen or methyl, $R^2$ represents carboxyl, cyano, carbamoyl, thiocarbamoyl, methoxycarbonyl or ethoxycarbonyl, $R^3$ represents hydrogen, chlorine or methyl, $R^4$ represents hydrogen, fluorine or chlorine, $R^5$ represents cyano, thiocarbamoyl, fluorine, chlorine, bromine or trifluoromethyl, and X represents methyl, ethyl, methoxy, ethoxy, methylthio, ethylthio, methoxycarbonyl or ethoxycarbonyl, each of which is substituted by methoxy, ethoxy, n- or i-propoxy, methyl-aminocarbonyl, ethylaminocarbonyl, n- or i-propylaminocarbonyl, dimethyl-aminocarbonyl, diethylaminocarbonyl, phenoxycarbonyl, benzyloxycarbonyl, phenylaminocarbonyl or benzylaminocarbonyl; or represents ethenyl which is substituted by methoxycarbonyl or ethoxycarbonyl.

7. A substituted phenyluracil according to claim 1 wherein n represents 1.

8. A substituted phenyluracil according to claim 1 wherein $R^2$ represents trifluoromethyl.

9. A substituted phenyluracil according to claim 1 wherein $R^4$ represents fluorine.

10. A substituted phenyluracil according to claim 1 wherein $R^5$ represents cyano or thiocarbamoyl.

11. A substituted phenyluracil of the formula (Ia)

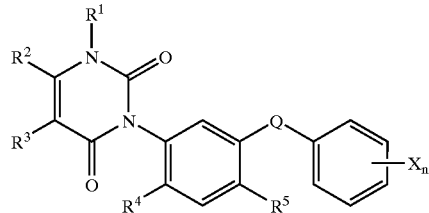

(Ia)

in which n, Q, $R^2$, $R^3$, $R^4$, and $R^5$ and X have the meaning given in claim 1.

12. A herbicidal composition comprising one or more of the phenyluracils of claim 1 and a member selected from the group consisting of extenders, surfactants and mixtures thereof.

13. A method of controlling undesired plants comprising applying an effective amount of one or more phenyluracils of claim 1 to said plants or their environment.

* * * * *